United States Patent [19]
Niklas

[11] 3,991,607
[45] Nov. 16, 1976

[54] HIGH RESOLUTION PULSE-ECHO ULTRASONIC METHOD AND APPARATUS
[75] Inventor: Ludwig Niklas, Lovenich, Germany
[73] Assignee: Krautkramer-Branson, Incorporated, Stratford, Conn.
[22] Filed: Sept. 8, 1975
[21] Appl. No.: 611,232

[52] U.S. Cl. .............................. 73/67.7; 73/67.8 R
[51] Int. Cl.² ......................................... G01N 29/04
[58] Field of Search ........... 73/67.7, 67.5 R, 67.8 R, 73/67.9, 71.5 US

[56] References Cited
UNITED STATES PATENTS
3,604,250  9/1971  Grandia ........................... 73/67.8 R
3,754,472  8/1973  Dory ................................. 73/67.9

Primary Examiner—Richard C. Queisser
Assistant Examiner—Stephen A. Kreitman
Attorney, Agent, or Firm—Ervin B. Steinberg; Philip J. Feig

[57]  ABSTRACT

Acoustic discontinuity responsive echo signals are compressed using special evaluating means for increasing the resolution of pulse-echo test apparatus. The acoustic discontinuity responsive echo signal undergoes mathematical convolution with a predetermined signal which latter signal is selected for providing that the mathematical product of the Laplace transform of the echo signal and the predetermined signal is unity. The mathematical convolution is performed by a computer, a correlator or an arrangement of delay lines.

23 Claims, 11 Drawing Figures

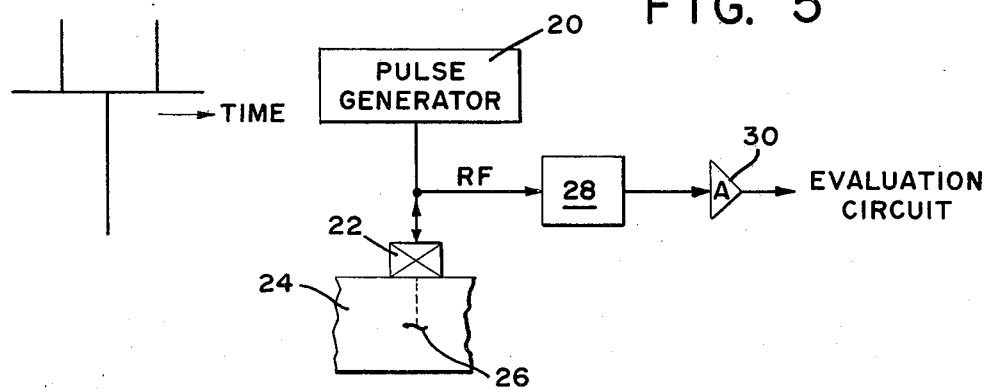
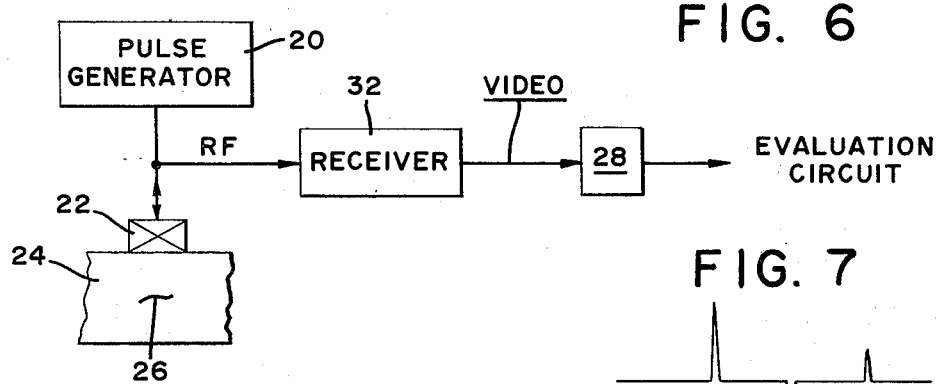
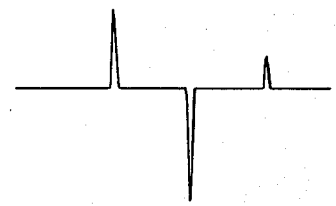
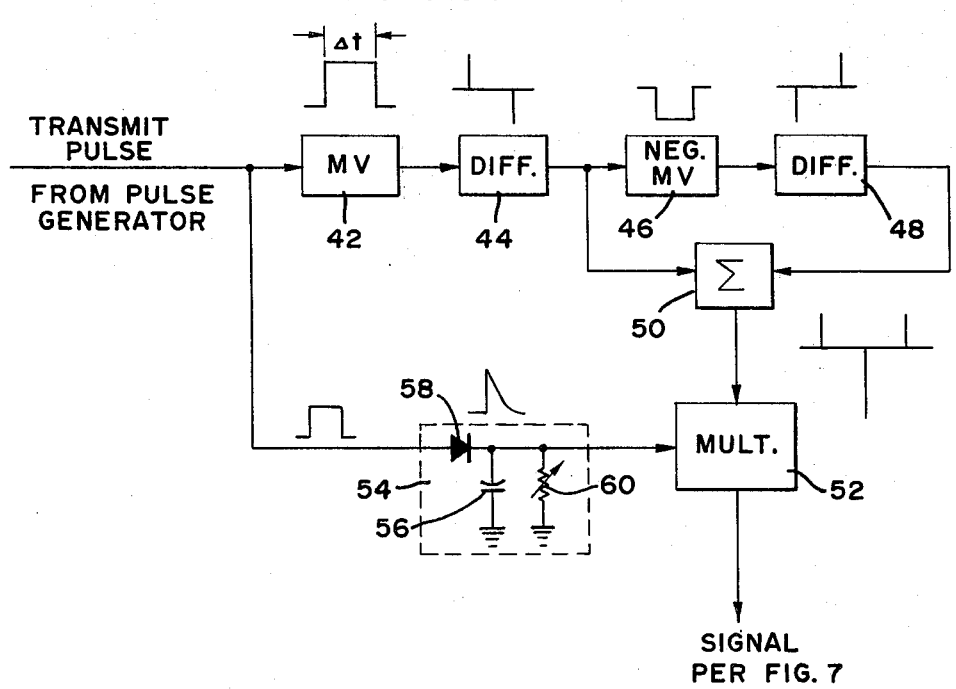

HIGH RESOLUTION PULSE-ECHO ULTRASONIC METHOD AND APPARATUS

BACKGROUND OF THE INVENTION

This invention refers to ultrasonic pulse-echo testing in which an ultrasonic search signal is transmitted cyclically from a transducer probe into a workpiece and the probe subsequently senses the receipt of echo signals arising from the search signal intercepting an acoustic discontinuity which reflects a portion of the transmitted acoustic energy.

As is well known to those skilled in the art great progress has been made in improving the resolution capability available using pulse-echo test apparatus with respect to small defects and defects disposed at relatively small distances from one another. These improvements are largely due to improved transducer construction and the replacement of electron tube amplifiers by transistorized amplifiers. Nevertheless, there is still a minimum distance in which a defect close to the workpiece surface cannot be resolved. This lack of resolution is due to the ringing of the transducer subsequent to it being pulsed for transmitting the search pulse, such ringing masking the echo signal. Also, if the transducer is excited by the receipt of a defect responsive acoustic signal, an immediately following similar defect responsive signal may be masked by the response of the transducer to the firstoccurring echo signal. Hence, the second defect responsive signal is not recognized. These cases clearly illustrate the lack of resolution still prevalent in currently used pulse-echo ultrasonic test apparatus.

In order to stop the ringing of the transducer probe after being excited by the transmit pulse, it has been proposed to immediately apply a pulse of opposite polarity so as to stop the oscillatory motion of the piezoelectric material. This method, by virtue of its complexity, has never been successful. Increased damping of the transducer by mechanical or electrical means obviously reduces its response to small signals and thereby decreases the transducer sensitivity. Similarly, pulse shortening circuits in the form of heretofore used filters decrease the sensitivity of the test apparatus and are of little usefulness in solving the problem of lack of resolution.

BRIEF SUMMARY OF THE INVENTION

The present invention reveals a new method and apparatus for increasing the resolution of pulse-echo test apparatus using special evaluating methods for compressing a pulse signal. In a practical embodiment, computer means or electrical circuit means are used to detect the receipt of a pulse signal and evaluate the signal without the use of suppression means. Resolution capability of pulses received within one period of the transmitted frequency is possible. Particularly, the present invention concerns itself with the detection of the receipt of a pulse in the time domain and the amplitude of the pulse during its first cycle and processing this information in the complete absence of suppression means. Ringing of the transducer as a function of the natural oscillatory decay is also of no consequence in the arrangement described hereafter.

For a better understanding of the present invention, reference is made to the following description and the illustrations forming a part thereof.

BRIEF DESCRIPTION OF THE DRAWINGS

FIG. 1 is a representation of a control voltage;
FIG. 5 is a schematic electrical circuit diagram pertaining to RF signal modification;
FIG. 6 is a schematic electrical circuit diagram pertaining to video signal modification;
FIG. 7 is a graphical representation of an electrical reference signal;
FIG. 8 is a schematic circuit diagram for generating the signal per FIG. 7.

DETAILED DESCRIPTION OF THE INVENTION

Figure 2:
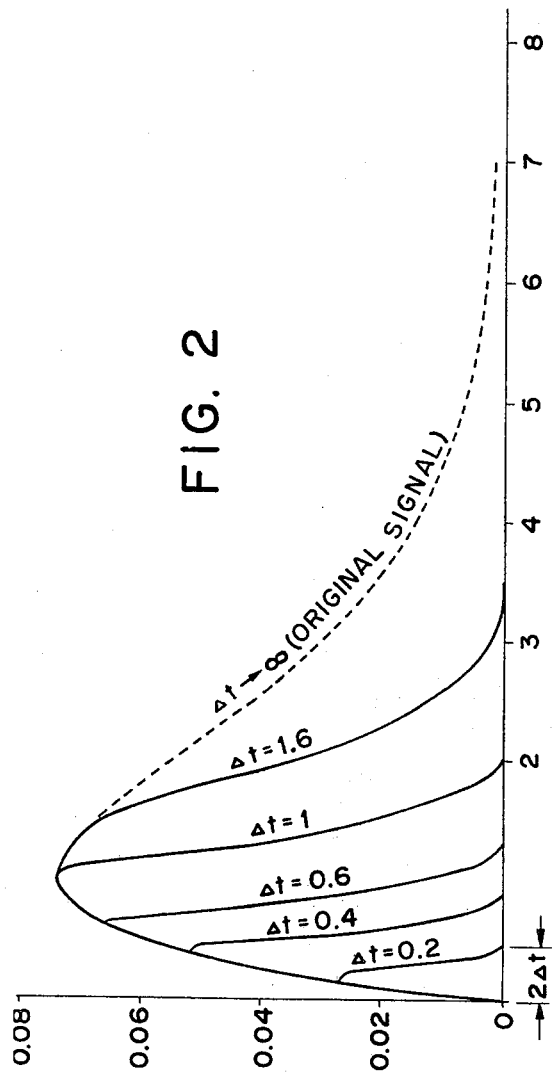
FIG. 2 is a graph of a modified video signal.

A. Echo Form:

An ultrasonic transducer probe comprising a piezoelectric element and a dampening mass contained in an enclosure or housing converts applied electric energy to ultrasonic energy and vice versa. If the probe is energized by a Dirac Delta pulse the effect is an exponentially decreasing wave train whose envelope has the form:

$$e^{-\alpha t}$$

wherein $\alpha$ is the attenuation of the probe and t is time.

The Laplace transform of the above function (FOURIER transform with $s = i\omega$) is $$\frac{1}{s+\alpha}$$

wherein $\omega = 2\pi f$ ($f$ = frequency) and $i$ = imaginary component ($\sqrt{-1}$).

If the probe is used as a transmitter and receiver, the Laplace transform of the echo-pulse envelope is the square of the above:

$$F(s) = 1/(s+\alpha)^2 \qquad (eq. 1)$$

In the time domain, equation 1 corresponds to the echo signal form (envelope):

$$f(t) = t e^{-\alpha t} \qquad (eq. 2)$$

and the high frequency (RF) pulse has the form $$f(t) = t e^{-\alpha t} \cos \omega_o t \qquad (eq. 3)$$

wherein $\omega_o = 2\pi f_0$ and $f_o$ = fundamental frequency of the probe.

Equation 3 omits ringing of the transducer front protective plate, ringing caused by any electrical matching coils in the transducer, ringing on account of incomplete sound isolation of the probe housing and ringing in the receiver amplifier.

B. Reduction of the Echo Signal Shape to Dirac δ-Pulse:

In order to obtain the signal reduction, the Laplace transform of the resulting pulse must be:

K(s)    1 (Laplace transform of the δ-pulse).

To this end, the Laplace transform of the echo-pulse per equation 1 is multiplied by a function G(s) so that:

$$K(s) = F(s) \cdot G(s) \quad 1 \quad \text{(eq. 4)}$$

In the time domain equation 4 corresponds to:

$$K(t) = \delta(t) = \int_0^t f(\tau) g(t-\tau) d\tau = f(t) * g(t) \quad \text{(eq. 5)}$$

(convolution integral)

To realize equation 5 it must be valid that:

$$G(s) = 1/F(s) = (s + \alpha)^2 \quad \text{(eq. 6)}$$

Generally for Laplace transforms, $$H(s + \alpha) \text{ corresponds to } e^{-\alpha t} h(t) \quad \text{(eq. 7)}$$

substituting $p = s + \alpha$, equation 6 then becomes:

$$G^*(p) = p^2;$$

in the time domain $$g^*(t) = \frac{d^2\delta(t)}{dt^2}$$

(second derivative of a δ-pulse)
combined with equation 7, the final result becomes:

$$g(t) = e^{-\alpha t} \frac{d^2\delta(t)}{dt^2} \quad \text{(eq. 8)}$$

The second derivative of a δ-pulse can be described by:

$$g(t) = e^{-\alpha t} \lim_{\Delta t \to 0} [\delta(t) - 2\delta(t-\Delta t) + \delta(t-2\Delta t)] \quad \text{(eq. 9)}$$

The expression contained in the square parentheses can be represented by a signal shown in FIG. 1.

C. Approximation of the Second Derivative of the δ-Pulse

For an approximation of the signal g(t) in equation 9 the limit is recalculated with a finite Δt being smaller than the pulse width of f(t); the resulting pulse when using this approximation is derived by inserting equation 9 in equation 5. Then:

$$k(t) = te^{-\alpha t} * e^{-\alpha t} [\delta(t) - 2\delta(t-\Delta t) + \delta(t - 2\Delta t)]. \quad \text{(eq. 10)}$$

Convolution with a δ-pulse reproduces the original function so that the final result will be:

$$k(t) = te^{-\alpha t} - 2e^{-\alpha \Delta t}(t-\Delta t)e^{-\alpha(t-\Delta T)} + e^{-2\alpha\Delta(t-2\Delta t)}e^{-\alpha(t-2\Delta t)} \quad \text{(eq. 11)}$$

wherein the second and the third term shall be zero if $(t-\Delta t)$ and $(t-2\Delta t)$ are less than or equal to 0.

When $t$ is greater than $2\Delta t$ equation 11 becomes:
$$k(t) = e^{-\alpha t} [t - 2(t-\Delta t) + (t-2\Delta t)] \equiv 0.$$

Conclusion

The described approximation shortens the original pulse $f(t) = te^{-\alpha t}$ to a time interval less than or equal to $2\Delta t$ since when $t$ is greater than $2\Delta t$ the ringing is exactly compensated to zero without the use of any non-linear suppression. FIG. 2 shows a graph of the original signal $te^{-\alpha t}$ for $\alpha = 1$ and $\Delta t$ being equal to the values 0.2, 0.4, 0.6, 1 and 1.6, the original function being shown as dotted.

If there are two pulses overlapping with a small transit time difference (two defects in close proximity to one another) they can be completely separated from each other by the present method if the transmit time difference is greater than $2\alpha t$.

However, the stated method will no longer work if the echo pulse overloads the amplifier, the output signal must be in the linear range of the amplifier which feature is readily achievable by proper amplifier design.

D. Compensation of the RF Signal (Equation 3 Using the Described Approximation)

The same method described above for the echo signal pulse can be applied also to the RF-signal per equation 3. The only difference is that there is a limited choice of Δt. If $\omega_o$ equals $2\pi f_o$, $f_o$ being the fundamental frequency, Δt must be a multiple of the half period $\frac{1}{2}f_o$. The signal g(t) corresponding to equation 9 must then assume the form:

$$g(t) = 1 \quad \text{for } t = 0$$
$$g(t) = -2e^{\frac{-\alpha k}{f_o}} \quad \text{for } t = k/f_o$$
$$g(t) = e^{\frac{-2\alpha k}{f_o}} \quad \text{for } t = 2k/f_o$$
$$g(t) = 0 \quad \text{for all other } t$$

wherein $k$ is any integer, $k = 1,2,3 \ldots$ (eq. 12)

or:

$$g(t) = 1 \quad \text{for } t = 0$$
$$g(t) = -2e^{\frac{-\alpha k}{f_o}} \quad \text{for } t = k/f_o$$
$$g(t) = e^{\frac{-2\alpha k}{f_o}} \quad \text{for } t = 2k/f_o$$
$$g(t) = 0 \quad \text{for all other } t$$

wherein $k$ is an odd multiple of $1/2$, $k = 1/2, 3/2, 5/2, \ldots$ (eq. 13)

Figure 3:
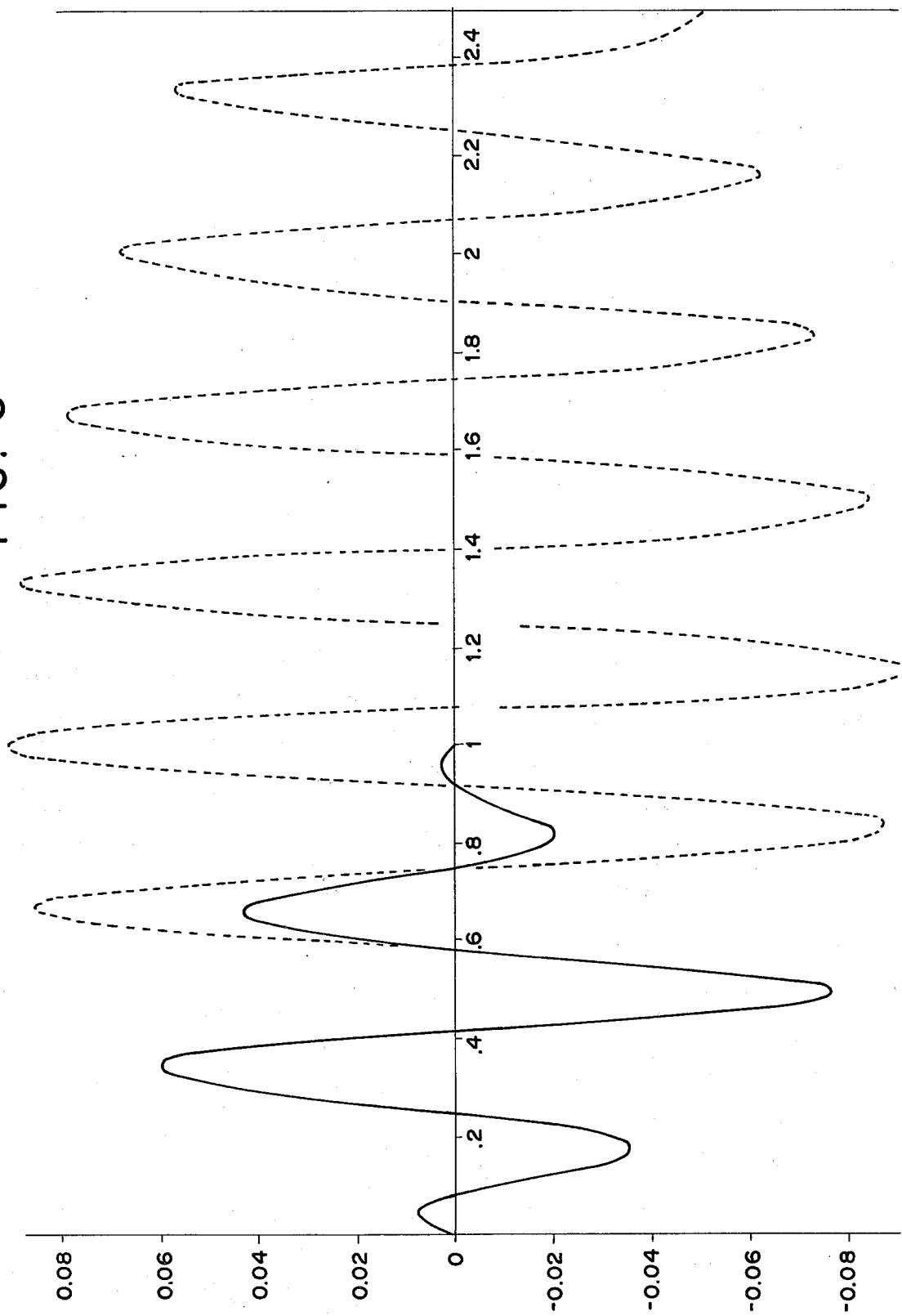
FIG. 3 is a graph of a modified RF signal.

FIG. 3 shows a graphical representation of the signals for $\alpha = 1$; $f_o = 3$; and $k = 1.5$. In accordance with the present method the long original pulse, shown by the dotted line, is shortened to three cycles.

Figure 4:
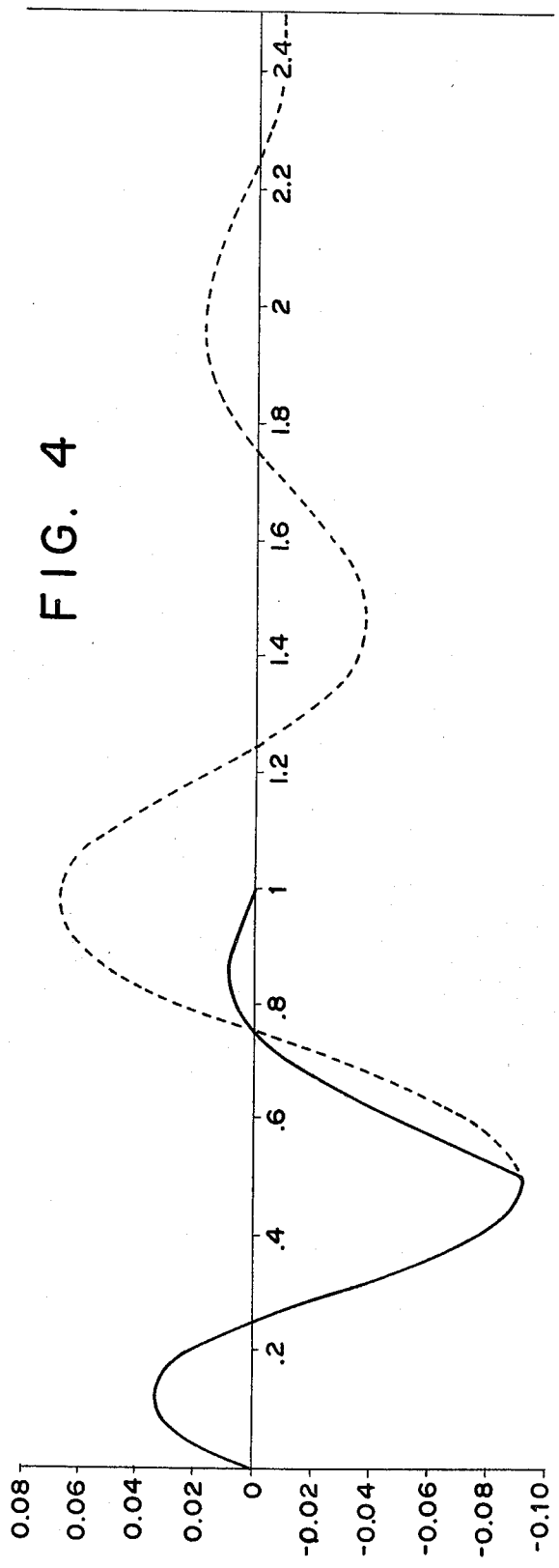
FIG. 4 is another graph of a signal.

FIG. 4 illustrates the reduction of a heavily, but not aperiodically, damped pulse (where $f_o = 1$ and $\alpha = 2$) to an ideal shock wave pulse ($k = 0.5$) using the described method.

The advantage to applying the above method to the RF pulse, in lieu of the envelope (video pulse) resides in the fact that this compensation can be effected in the first amplifier stages or at the transducer probe where the echo pulses do not overload the amplifier. A disadvantage resides in the fact that the value of Δt must be precisely calibrated to the transducer probe frequency $f_o$.

E. Practical Embodiments of Pulse Shortening Method

As has been indicated heretofore the pulse shortening method described can be applied to the RF signal or the video signal.

Referring to FIG. 5, a pulse generator 20 cyclically applies to a transducer probe 22 a RF pulse electrical signal. The probe converts the electrical signal to an ultrasonic search signal which is transmitted into the workpiece 24 where the search signal intercepts a defect 26. A resultant echo signal sensed by the probe 22 is converted to an electrical signal and is conducted to the pulse shortening circuit 28 having means which will be described below wherein the RF signal wave train is shortened using the principle heretofore described. From the circuit 28, the shortened signal is transmitted to an amplifier 30 and then to a known evaluation circuit, such as a cathode ray tube display or a logic circuit, etc.

FIG. 6 depicts a similar arrangement except that the pulse shortening means 28 is coupled to receive the video signal from the receiver circuit 32.

Using a digital minicomputer for the embodiment per FIG. 6, the computer replaces the pulse shortening means 28. The received echo signal is conducted to an input connector coupled to an analog to digital converter for converting the analog echo responsive signal into a digital format signal. The computer is programmed to solve the equation 11. This is accomplished by storing the first term, the original non-compensated signal in the computer memory, shifting the argument by $\Delta t$ and multiplying by a factor of two (zero for negative arguments) and subtracting the value from the memory, then shifting the original signal by $2\Delta t$ and adding that value to the memory. The resulting signal stored in the memory is the solution of equation 11. For high resolution the increment $\Delta t$ is selected to be small taking into account the resulting lower sensitivity. For increasing the sensitivity $\Delta t$ is selected to be greater, however, as $\Delta t$ approaches unity the resolution is decreased.

In the embodiment where the RF signal is processed using the arrangement depicted in FIG. 5, $\Delta t$ must be selected to be a multiple of $1/f_o$ or an odd multiple half of $1/f_o$, see equation 13. In the latter case all of the three terms per the equation must be added together.

Another alternative solution comprises the use of a computer which is programmed for solving the convolution integral per equation 5 wherein $f(t)$ is the non-compensated echo signal and the value $g(t)$ is programmed in the computer as per equation 12 or equation 13 (RF signal). Computers for this type of operation are available commercially under the name of "correlators". Equation 5 is identical with a cross correlation function and the correlator is programmed for solving the equation 5. The signal from the transducer probe is provided as a first input to the correlator comprising the term $f(t)$ and the correlator receives at a second input a reference signal comprising the term $g(t)$ which corresponds either to equation 12 or 13. The electrical signal $g(t)$ per equation 12 must be the triple pulse as shown in FIG. 7. This signal is generated by a circuit as shown in FIG. 8.

The transmit pulse is applied to a multivibrator 42 and the output from the multivibrator 42 is conducted to a differentiator 44. The differentiator output is fed to a negative multivibrator 46 and the output from the negative multivibrator to a differentiator 48. A summation network combines the outputs from the differentiators 44 and 48 to provide a signal with two spaced positive peaks and a centrally disposed negative peak of double amplitude. A signal decay circuit 54 receives its input from the pulse generator for charging the capacitor 56 via rectifier 58 to a positive peak value. The resistor 60 adjusts the decay rate. Multiplier 52 receives the signal from the circuit 54 and from the summation circuit 50 to provide the signal of shape per FIG. 7.

For equation 13 the negative multivibrator 46 must be a positive multivibrator.

Delay Line Circuits

If any pulse f(t) is passed through a filter whose impulse response corresponds to g(t) the filter output is given by the convolution integral of equation 5. This means that the output from the filter is identical with the compensated pulse signal $k(t)$ when the filter impulse response corresponds to equations 12 or 13. Such a filter can be inserted readily between the transducer probe receiving the echo signal and the amplifier.

A filter having this characteristic can be realized by the use of delay lines. Several possibilities present themselves.

Figure 9:
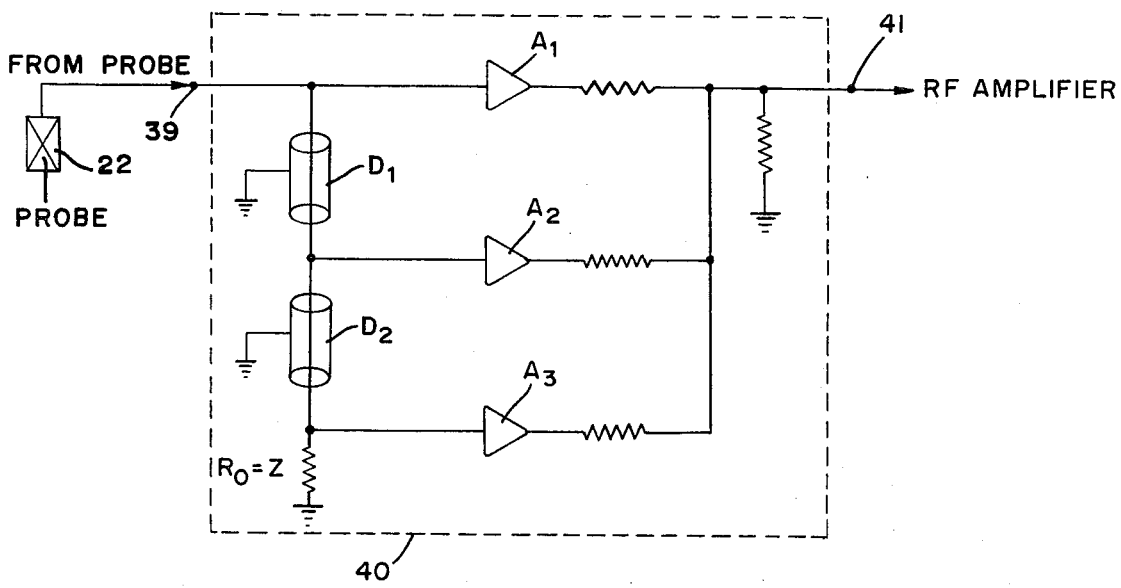
FIG. 9 is a schematic circuit diagram disclosing delay lines for signal modification.

A typical embodiment is shown in FIG. 9. The ultrasonic transducer probe 22 is coupled to the input connection 39 of a circuit comprising two delay lines $D_1$ and $D_2$, and three matched amplifiers $A_1$, $A_2$ and $A_3$. The delay lines $D_1$ and $D_2$ have a travel time $k/f_o$ as shown in equations 12 and 13 (applicable to RF signals) and are matched on the end of an impedance $R_0 = Z$ ($Z$ is the impedance of the delay line) so that no reflection will occur. If the preamplifier $A_1$ has a gain of $g_1$, the gain of the other amplifiers must correspond to $$g_2 = g_1 \cdot 2e^{\frac{-\alpha k}{f_o}}$$
and
$$g_3 = g_1 \cdot e^{\frac{-2\alpha k}{f_o}}$$

whereby for $k =$ integer, the amplifier $A_2$ must phase inverting. If $k$ equals odd multiples of ½, amplifier $A_2$ must be non-phase inverting. The outputs of the three preamplifiers $A_1$, $A_2$ and $A_3$ are added together at output connection 41 and provided to the main RF amplifier.

Figure 10:
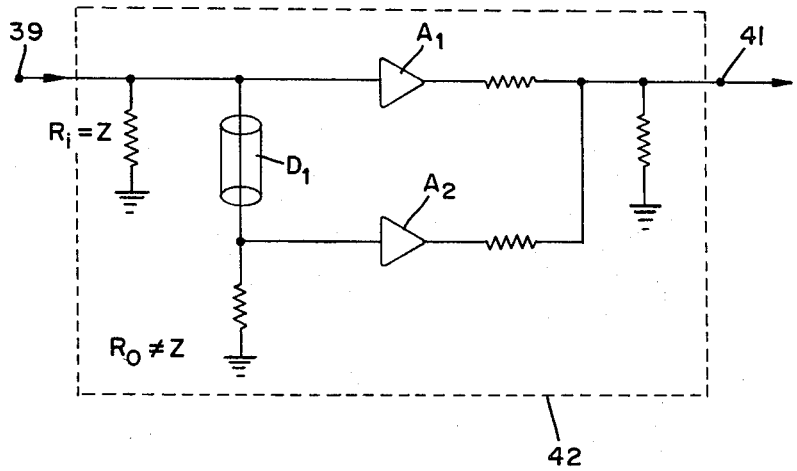
FIG. 10 is another schematic circuit diagram disclosing the use of a single delay line for signal modification.

FIG. 10 shows a simplification of the arrangement per FIG. 9. In circuit 42 only one delay line $D_1$ is used. The delay line $D_2$ of circuit per FIG. 9 has been replaced in FIG. 10 by a reflection at the end of delay line $D_1$. For this purpose the end of delay line $D_1$ is mismatched by an impedance $R_o \neq Z$ so that the reflection factor is $$e^{\frac{-2\alpha k}{f_o}}$$

but the input of $D_1$ is matched so $R_i = Z$ to cause the first and third pulse of $g(t)$ per FIG. 7 to be provided at the amplifier $A_1$, and the second pulse to be provided to amplifier $A_2$ as previously.

Figure 11:
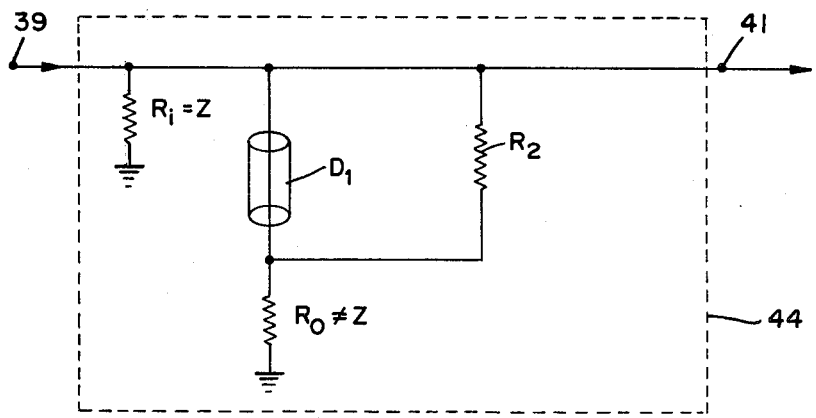
FIG. 11 is another schematic circuit diagram similar to FIG. 10 applicable to certain signal conditions.

FIG. 11 depicts a further alternative circuit which can be used successfully only if the attenuation of the transducer probe is high. The circuit 44 is a simplified passive filter and operates similar to the circuit per FIG. 10 described above. In circuit 44 the second pulse of g(t) is added by bypassing delay line $D_1$. Impedance $R_2$ is selected to cause the second pulse to have an amplitude $$2e^{\frac{-\alpha k}{f_o}}.$$

Aside from the desired pulses there are additional pulses caused by multiple reflection in delay line $D_1$. However, if the attenuation of the probe is sufficiently high the multiple reflections have a much lower amplitude than the first three desired pulses for providing a sufficiently close approximation of the result.

What is claimed is:

1. The method of evaluating in a pulse-echo ultrasonic arrangement an acoustic discontinuity responsive echo signal comprising: receiving an acoustic discontinuity responsive echo signal and converting said echo signal to an electrical signal, and processing said electrical signal by electronically performing a mathematical convolution of said electrical signal with a predetermined signal, said predetermined signal being selected such that the mathematical product of the Laplace transform of said electrical signal and of said predetermined signal equals unity, for providing a signal having a duration beginning substantially with the receipt of said electrical signal and terminating prior to the natural decay of said electrical signal.

2. The method of evaluating in a pulse-echo ultrasonic arrangement an acoustic discontinuity response echo signal comprising: energizing an electroacoustic transmit-receive probe coupled to a workpiece with a narrow pulse width pulse for transmitting ultrasonic energy into the workpiece;

receiving at said probe an echo responsive acoustic signal responsive to an acoustic discontinuity in the workpiece and converting said acoustic signal to a radio frequency (RF) electrical signal, and processing said RF electrical signal by electrically performing a mathematical convolution of said RF electrical signal with a predetermined signal, said predetermined signal being selected such that the mathematical product of the Laplace transform of said RF electrical signal and of said predetermined signal equals unity for providing a signal having a duration beginning substantially with the receipt of said RF electrical signal and terminating prior to the natural decay of said RF electrical signal.

3. The method of evaluating in a pulse-echo ultrasonic arrangement an acoustic discontinuity responsive echo signal as set forth in claim 2, convolving said RF electrical signal with a predetermined signal of the form:

$g(t) = 1$     for $t = 0$ $g(t) = 2e^{\frac{-\alpha k}{f_o}}$     for $t = k/f_o$ $g(t) = e^{\frac{-2\alpha k}{f_o}}$     for $t = 2k/f_o$ $g(t) = 0$     for all other $t$ wherein, $k$ is an odd multiple of one-half (such as ½, 3/2, 5/2, ...), $\alpha$ is the attenuation of the probe, and $f_o$ is the fundamental frequency of the probe.

4. The method of evaluating in a pulse-echo ultrasonic arrangement an acoustic discontinuity responsive echo signal as set forth in claim 2, convolving said RF electrical signal with a predetermined signal of the form:

$g(t) = 1$     for $t = 0$ $g(t) = -2e^{\frac{-\alpha k}{f_o}}$     for $t = k/f_o$ $g(t) = e^{\frac{-2\alpha k}{f_o}}$     for $t = 2k/f_o$ $g(t) = 0$     for all other $t$ wherein, $k$ is an integer (such as 1, 2, 3, ...), $\alpha$ is the attenuation of the probe, and $f_o$ is the fundamental frequency of the probe.

5. The method of evaluating in a pulse-echo ultrasonic arrangement an acoustic discontinuity responsive signal as set forth in claim 2, electrically performing a mathematical convolution of said electrical RF electrical signal by:

conducting said RF electrical signal through a first delay line having a travel time $k/f_o$, wherein k is an odd multiple of one-half, (such as ½, 3/2, 5/2, ...), and $f_o$ is the fundamental frequency of the probe, for providing a first signal;

conducting said first signal through a second series connected delay line having a travel time $k/f_o$ and terminated in an impedance equal to the impedance of said delay line for providing a second signal;

amplifying said RF electrical signal by a predetermined factor for providing a third signal;

amplifying said first signal by $$2e^{\frac{-\alpha k}{f_o}}$$

times said predetermined factor for providing a fourth signal, wherein $\alpha$ is the attenuation of the probe;

amplifying said second signal by $$e^{\frac{-2\alpha k}{f_o}}$$

times said predetermined factor for providing a fifth signal, and adding said third signal, said fourth signal and said fifth signal for providing an output signal having a duration beginning substantially with the receipt of said RF electrical signal and terminating prior to the natural decay of said electrical signals.

6. The method of evaluating in a pulse-echo ultrasonic arrangement an acoustic discontinuity responsive echo signal as set forth in claim 2, electrically performing a mathematical convolution of said electrical signal by:

conducting said RF electrical signal through a first delay line having a travel time $k/f_o$, wherein $k$ is an integer (such as 1, 2, 3 ...), and $f_o$ is the fundamental frequency of the probe, for providing a first signal;

conducting said first signal through a second series connected delay line having a travel time $k/f_o$ and terminated in an impedance equal to the impedance of said delay line for providing a second signal;

amplifying said electrical signal by a predetermined factor for providing a third signal;

amplifying said first signal by $$2e^{\frac{-\alpha k}{f_o}}$$

times said predetermined factor, for providing a fourth signal, wherein $\alpha$ is the attenuation of the probe;

amplifying said second signal by $$e^{\frac{-2\alpha k}{f_o}}$$

times said predetermined factor for providing a fifth signal, and adding said third signal and said fifth signal and subtracting said fourth signal for providing an output signal responsive to said acoustic signal.

7. The method of evaluating in a pulse-echo ultrasonic arrangement an acoustic discontinuity responsive echo signal as set forth in claim 2, electrically performing a mathematical convolution with said electrical signal by:

terminating the output of a delay line with an impedance such that the reflection coefficient is $$e^{\frac{-2\alpha k}{f_o}},$$

wherein $k$ is an integer, $f_o$ is the fundamental frequency of the probe and $\alpha$ is the attenuation of the probe;

terminating the input of said delay line with an impedance equal to the impedance of said delay line;

conducting said RF electrical signal through said delay line for providing a first signal at the output of said delay line and a reflected signal back at the input of said delay line;

providing said electrical signal and said reflected signal to a first amplifier of predetermined gain for providing a second signal responsive to the sum of said electrical signal and said reflected signal;

providing said first signal to an inverting amplifier having a gain twice that of the first amplifier for providing a third signal, and adding said second signal and said third signal for providing an output signal responsive to said acoustic signal.

8. The method of evaluating in a pulse-echo ultrasonic arrangement an acoustic discontinuity responsive echo signal as set forth in claim 2, electrically performing a convolution with said electrical signal by:

terminating the output of a delay line in an impedance such that the reflection coefficient is $$e^{\frac{-2\alpha k}{f_o}}$$

wherein $\alpha$ is the attenuation of the probe, $k$ is an odd multiple of one-half (such as ½, 3/2, 5/2, ...), and $f_o$ is the fundamental frequency of the probe;

terminating the input of said delay line with an impedance equal to the impedance of said delay line;

conducting said RF electrical signal through said delay line for providing a first signal at the output of said delay line and a reflected signal at the input of said delay line;

attenuating said first signal such that the first signal is amplified by a factor $$2e^{\frac{-\alpha k}{f_o}},$$

and combining said electrical signal, said reflected signal and said attenuated said first signal for providing an output signal responsive to said acoustic signal.

9. The method of evaluating in a pulse-echo ultrasonic arrangement an acoustic discontinuity responsive echo signal as set forth in claim 2, electrically performing a mathematical convolution of said RF electrical signal by:

storing said RF electrical signal in a computer memory;

shifting the argument of said electrical signal by a first predetermined quantity ($\Delta t$) commensurable with the value $1/2f_o$, wherein $f_o$ is the fundamental frequency of the probe and multiplying the signal by a factor of two and storing the resultant signal in the computer as a first signal;

shifting the argument of said electrical signal by a second predetermined quantity ($2\Delta t$) and storing the resultant signal in the computer as a second signal, and combining said electrical signal said first signal and said second signal for providing an output signal having a duration beginning substantially with the receipt of said electrical signal and terminating prior to the natural decay of said electrical signal.

10. The method of evaluating in a pulse-echo ultrasonic arrangement an acoustic discontinuity responsive echo signal as set forth in claim 2, electrically performing a mathematical convolution of said RF electrical signal by:

storing said RF electrical signal in a computer memory;

shifting the argument of said electrical signal by a first predetermined quantity ($\Delta t$) commensurable with the value $1/f_o$, wherein $f_o$ is the fundamental frequency of the probe and multiplying the signal by a factor of two and storing the resultant signal in the computer as a first signal;

shifting the argument of said electrical signal by a second predetermined quantity ($2\Delta t$) and storing the resultant signal in the computer as a second signal, and adding said electrical signal and said second signal and subtracting said first signal for providing an output signal having a duration beginning substantially with the receipt of said electrical signal and terminating prior to the natural decay of said electrical signal.

11. The method of evaluating in a pulse-echo ultrasonic arrangement an acoustic discontinuity responsive echo signal comprising:

energizing an electroacoustic transmit-receive probe with a narrow pulse width pulse for transmitting ultrasonic energy into a workpiece;

receiving an echo responsive acoustic signal from the workpiece and converting said acoustic signal to an RF electrical signal;

conducting said RF electrical signal to a receiver circuit for converting said RF electrical signal into a video electrical signal, and processing said video electrical signal by electrically performing a mathematical convolution of said video electrical signal with a predetermined signal, said predetermined signal being selected such that the mathematical product of the Laplace transform of said video electrical signal and of said predetermined signal equals unity for providing a signal having a duration beginning substantially with the receipt of said video electrical signal and terminating prior to the natural decay of said electrical signal.

12. The method of evaluating in a pulse-echo ultrasonic arrangement an acoustic discontinuity responsive echo signal as set forth in claim 11, electrically performing a mathematical convolution of said video electrical signal by:

storing said electrical signal in a computer memory;

shifting the argument of said electrical signal by a first predetermined quantity ($\Delta t$) less than the pulse width of said electrical signal and multiplying the signal by a factor of two and storing the resultant signal in the computer as a first signal:

shifting the argument of said electrical signal by a second predetermined quantity ($2\Delta t$) and storing the resultant signal in the computer as a second signal, and combining said video electrical signal and said second signal and subtracting said first signal for providing an output signal having a duration beginning substantially with the receipt of said electrical signal and terminating prior to the natural decay of said electrical signal.

13. An apparatus for use in a pulse-echo ultrasonic test arrangement for evaluating an acoustic discontinuity responsive echo signal comprising:

an electroacoustic probe for transmitting when energized ultrasonic energy into a workpiece and receiving acoustic discontinuity responsive echo signals therefrom;

a pulse generator coupled to said probe for cyclically energizing said probe;

a network coupled to said probe for receiving said acoustic discontinuity responsive echo signal and electrically performing a mathematical convolution of said acoustic discontinuity responsive echo signal with a predetermined signal, said predetermined signal being selected such that the mathematical product of the Laplace transform of said acoustic discontinuity responsive echo signal and said predetermined signal equals unity for providing an output signal having a duration beginning substantially with the receipt of said acoustic discontinuity responsive echo signal and terminating prior to the natural decay of said acoustic discontinuity responsive echo signal.

14. An apparatus as set forth in claim 13 said network having an input connection and an output connection and comprising the series connection of a first delay line $D_1$, coupled with its input connection to the input connection of said network, a second delay line $D_2$ and an impedance $R_o$ serially connected between the output terminal of said delay line $D_2$ and a common potential, a first amplifier $A_1$ having a predetermined gain coupled between said input connection of said network and said output connection of said network, a second amplifier $A_2$ phase inverting coupled between the connection serially connecting said first delay line to said second delay line and said output connection of said network, and a third amplifier $A_3$ coupled between said connection serially connecting said second delay line to said resistance $R_o$ and said output connection of said network wherein said delay lines having a travel time $k/f_o$, $k$ is an integer (such as 1, 2, 3, . . . ), and $f_o$ is the fundamental frequency of the probe, the gain of said second amplifier $A_2$ is $$2e^{\frac{-\alpha k}{f_o}}$$

times said predetermined gain of amplifier $A_1$ and the gain of said amplifier $A_3$ is $$e^{\frac{-2\alpha k}{f_o}}$$

times said predetermined gain of said amplifier $A_1$ wherein $\alpha$ is the attenuation of the probe.

15. An apparatus as set forth in claim 13, said network having an input connection and an output connection and comprising: an input impedance $R_i$ coupled between said input connection of said network and a common potential, a first amplifier $A_1$ having a predetermined gain coupled between said input connection and said output connection of said network, a delay line coupled between said input connection of said network and a first terminal of an impedance $R_o$ the other terminal of the impedance $R_o$ is connected to common potential, a second amplifier, phase inverting, $A_2$ coupled between the connection connecting said delay line and said impedance $R_o$ and said output connection of said network, wherein said input impedance $R_i$ is equal to the impedance of said delay line, said impedance $R_o$ is selected such that the reflection coefficient of said delay line is $$e^{\frac{-2\alpha k}{f_o}}.$$

wherein $k$ is an integer, $\alpha$ is the attenuation of the probe and $f_o$ is the fundamental frequency of the probe, the gain of said second amplifier $A_2$ being twice the predetermined gain of said first amplifier $A_1$.

16. An apparatus as set forth in claim 13, said network having an input connection and an output connection comprising an input impedance $R_i$ coupled between said input connection and output connection of said network and common potential, a delay line serially connected to an output impedance $R_o$ between said input connection and said output connection of said network and common potential, an impedance $R_2$ coupled between the connection serially connecting said delay line and said output impedance $R_o$ and said input connection and said output connection of said network, wherein said impedance $R_i$ is selected to be equal to the impedance of said delay line, said impedance $R_o$ is selected for causing the reflection coefficient of said delay line to be $$e^{\frac{-2\alpha k}{f_o}}$$

wherein $\alpha$ is the attenuation of the probe, $k$ is an odd multiple of one-half (such as ½, 3/2, 5/2, . . . ), and $f_o$ is the fundamental frequency of the probe said impedance $R_2$ is selected for causing the pulse traveling through said delay line to be amplified by a factor $$2e^{\frac{-\alpha k}{f_o}}$$

17. An apparatus as set forth in claim 13, said network having an input connection and an output connection and comprising;
    converter means coupled to said input connection for converting said acoustic discontinuity responsive signal into a digital signal;
    digital computing means coupled to said converter means for receiving said digital signal and programmed for storing said digital signal, shifting the argument of said digital signal by an amount $\Delta t$, commensurate with the value $\frac{1}{2}f_o$ wherein $f_o$ is the fundamental frequency of the probe, multiplying the resultant signal by a factor of two and storing said signal as a first signal, shifting the argument of said digital by an amount of $2\Delta t$ and storing the resultant signal as a second signal, mathematically combining said digital signal, said first signal and said second signal for providing an output signal said output signal being coupled to said output connection.

18. An apparatus as set forth in claim 13, said network having an input connection and an output connection and comprising;
    converter means coupled to said input connection for converting said acoustic discontinuity responsive signal into a digital signal;
    digital computing means coupled to said converter means for receiving said digital signal and programmed for shifting said digital signal by an amount $\Delta t$, commensurate with the value $\frac{1}{2}f_o$ wherein $f_o$ is the fundamental frequency of the probe, multiplying the resultant signal by a factor of two and storing said signal as a first signal, shifting the argument of said digital signal by an amount $2\Delta t$ and storing the resultant signal as a second signal, mathematically adding said digital signal and said second signal and subtracting said first signal for providing an output signal said output signal being coupled to said output connection.

19. An apparatus for use in a pulse-echo ultrasonic test arrangement for evaluating an acoustic discontinuity responsive echo signal comprising:
    an electroacoustic probe for transmitting when energized ultrasonic energy into a workpiece and receiving acoustic discontinuity responsive echo signals therefrom;
    a pulse generator coupled to said probe for cyclically energizing said probe;
    a receiver coupled to said probe for receiving said acoustic discontinuity responsive echo signals and converting said signals into video electrical signals, and
    a network coupled to said probe for receiving said video electrical signal and electrically performing a mathematical convolution of said video electrical signal with a predetermined signal, said predetermined signal being selected such that the mathematical product of the Laplace transform of said video electrical signal and said predetermined signal equals unity for providing an output signal having a duration beginning substantially with the receipt of said video electrical signal and terminating prior to the natural decay of said video electrical signal.

20. An apparatus as set forth in claim 19, said network having an input connection and an output connection and comprising;
    converter means coupled to said input connection for converting said video electrical signal into a digital signal;
    digital computing means coupled to said converter means for receiving said digital signal and programmed for storing said digital signal, shifting the argument of said digital signal by an amount $\Delta t$, less than the pulse width of said electrical signal, multiplying the resultant signal by a factor of two and storing said signal as a first signal, shifting the argument of said digital signal by an amount $2\Delta t$ and storing the resultant signal as a second signal, mathematically combining said digital signal and said second signal and subtracting said first signal for providing an output signal said output signal being coupled to said output connection.

21. An apparatus for use in a pulse-echo ultrasonic test arrangement for evaluating an acoustic discontinuity responsive echo signal comprising:
    an electroacoustic probe for transmitting when energized ultrasonic energy into a workpiece and receiving acoustic discontinuity responsive echo signals therefrom;
    a pulse generator coupled to said probe for cyclically energizing said probe;
    means for providing a predetermined signal having a characteristic such that the mathematical product of the Laplace transform of said acoustic discontinuity responsive echo signal and said predetermined signal equals unity, and
    an electrical circuit network coupled to said probe for receiving said acoustic discontinuity responsive echo signal and coupled to said means for providing said predetermined signal for receiving said predetermined signal and electrically performing a mathematical convolution of said acoustic discontinuity responsive echo signal with said predetermined signal for providing an output signal having a duration beginning substantially with the receipt of said acoustic discontinuity responsive echo signal and terminating prior to the natural decay of said acoustic discontinuity responsive echo signal.

22. An apparatus as set forth in claim 21, said network having an input connection and an output connection and comprising:
    a correlator having two input terminals, one input terminal coupled to said input connection for receiving said acoustic discontinuity responsive signal;
    said second input terminal of said correlator coupled to said means for providing a predetermined signal for receiving said predetermined signal of the form:

$g(t) = 1$      for $t = 0$ $g(t) = 2e^{\frac{-\alpha k}{f_o}}$      for $t = k/f_o$ $g(t) = e^{\frac{-2\alpha k}{f_o}}$      for $t = 2k/f_o$ $g(t) = 0$      for all other $t$ wherein $k$ is an odd multiple of one-half (such as ½, 3/2, 5/2, . . . ), $\alpha$ is the attenuation characteristic of the probe, and $f_o$ is the fundamental frequency of the probe, and means coupling said correlator to said output connection of said network for providing an output signal responsive to the cross-correlation of said acoustic discontinuity responsive signal and said predetermined signal.

23. An apparatus as set forth in claim 21, said network having an input connection and an output connection and comprising:

a correlator having two input terminals one input terminal coupled to said input connection for receiving said acoustic discontinuity responsive signal;

said second input terminal of said correlator coupled to said means for providing a predetermined signal for receiving said predetermined signal of the form:

$$g(t) = 1 \quad \text{for } t = 0$$
$$g(t) = -2e^{\frac{-\alpha k}{f_o}} \quad \text{for } t = k/f_o$$
$$g(t) = e^{\frac{-2\alpha k}{f_o}} \quad \text{for } t = 2k/f_o$$
$$g(t) = 0 \quad \text{for all other } t$$

wherein $k$ is an integer, $\alpha$ is the attenuation characteristic of the probe and $f_o$ is the fundamental frequency of the probe, and said correlator coupled to said output connection of said network for providing an output signal responsive to the cross-correlation of said acoustic discontinuity responsive signal and said predetermined signal.

* * * * *

UNITED STATES PATENT OFFICE
CERTIFICATE OF CORRECTION

PATENT NO. : 3,991,607
DATED : November 16, 1976
INVENTOR(S) : Ludwig Niklas

It is certified that error appears in the above-identified patent and that said Letters Patent are hereby corrected as shown below:

Column 3, line 3, should read: $K(s) \equiv 1$ (Laplace transform of the $\delta$-pulse)

line 7, should read: $K(s) = F(s) \cdot G(s) \equiv 1$     (eq. 4)

line 37, should read:
$$g(t) = e^{-\alpha t} \frac{d^2 J(t)}{dt^2} \quad (eq. 8)$$

lines 63-64, should read:
$$K(t) = t e^{-\alpha t} - 2 e^{-\alpha \Delta t}(t-\Delta t) e^{-\alpha(t-\Delta t)} + e^{-2\alpha \Delta t}(t-2\Delta t) e^{-\alpha(t-2\Delta t)} \quad (eq. 11)$$

Column 4, line 14, "transmit" should be --transit--;

line 15, "2$\alpha$t" should be --2$\Delta$t--;

line 42, should read:
$$g(t) = 2 e^{-\frac{\alpha K}{f_0}} \text{ for } t = K/f_0$$

Column 6, line 28, "of" should be --by--.

Column 7, line 27, "response" should be --responsive--.

Column 10, line 29, insert comma (,) between "signal and "said first".

Column 13, line 21, after "digital" insert --signal--.

Signed and Sealed this

Eighth Day of February 1977

[SEAL]

Attest:

RUTH C. MASON
*Attesting Officer*

C. MARSHALL DANN
*Commissioner of Patents and Trademarks*